United States Patent [19]
Towart et al.

[11] Patent Number: 6,147,094
[45] Date of Patent: Nov. 14, 2000

[54] REDUCTION OF CARDIOTOXICITY OF AN ANTITUMOR AGENT USING MANGANESE COMPOUND

[75] Inventors: Robertson Towart, Stoke Poges, United Kingdom; Jan O. G. Karlsson, Nesoddtangen; Per Jynge, Trondheim, both of Norway

[73] Assignee: Nycomed Imaging AS, Oslo, Norway

[21] Appl. No.: 09/213,246

[22] Filed: Dec. 17, 1998

Related U.S. Application Data

[63] Continuation of application No. PCT/GB97/01721, Jun. 24, 1997.

[30] Foreign Application Priority Data

Jun. 24, 1997 [GB] United Kingdom .................. 9613182

[51] Int. Cl.⁷ ........................... A61K 31/44; A61K 31/70
[52] U.S. Cl. .............................. 514/332; 514/34; 514/836
[58] Field of Search ............................... 514/34, 332, 836

[56] References Cited

U.S. PATENT DOCUMENTS 4,138,480   2/1979   Gosalvez ................................ 424/180

OTHER PUBLICATIONS

Lee et al., Diss. Abst. Int(Sci.), 46(10):3396 (1986).
Carswell, JAMA, 248(31):814–819 (1982).
Brurok, Invest. Radiol., 30(3):159–167 (1995).

*Primary Examiner*—Theodore J. Criares
*Attorney, Agent, or Firm*—Bacon & Thomas

[57] ABSTRACT

The invention relates to the use of certain chelating agents and their metal chelates and to the use of certain manganese containing compounds, in particular manganese chelates, in the manufacture of a therapeutic agent for use in reducing the cardiotoxicity of an antitumor agent. Such compounds are particularly effective in reducing the side-effects of anthracycline drugs and/or paclitaxel.

8 Claims, 6 Drawing Sheets

REDUCTION OF CARDIOTOXICITY OF AN ANTITUMOR AGENT USING MANGANESE COMPOUND

This application is a continuation application of international application No. PCT/GB97/01721 filed Jun. 24, 1997, of which the entire disclosure of the prior application is hereby incorporated by reference.

BACKGROUND OF THE INVENTION

1. Field of the Invention

The present invention relates to the use of chelating agents and their metal chelates and to the use of certain manganese containing compounds, in particular manganese chelates, in medicine. In particular, the invention relates to the use of such compounds in anti-tumour therapy.

2. Description of the Related Art

A number of anti-tumor agents are associated with adverse side-effects which severely limit their widespread use. Paclitaxel or taxol is one such agent which has shown anti-neoplastic action against a variety of malignant tissues, including those of the breast, colon, lung and ovary as well as in malignant melonoma. However, at the high dosages required to have an anti-neoplastic effect, paclitaxel has a number of adverse side-effects which can include cardiovascular irregularities as well as hematological and gastrointestinal toxicity.

Anthracycline antibiotics, such as doxorubicin (adriamycin), are amongst the most important of the anti-tumour agents. However, their clinical value is limited by their cardiotoxicity, which manifests itself as congestive heart failure in 15–40% of patients undergoing therapy. The most likely mechanism for their toxicity is believed to be the production of oxygen-derived free radicals in the heart, which cause membrane damage and mitochondrial damage in metabolically active tissues such as heart muscle and intestinal mucosa.

There is evidence to suggest that cardiac damage during anthracycline therapy can be reduced by simultaneous administration of the iron chelator, dexrazoxane (Goodman & Gilman, 9th ed. 1233–1287 (1996)). However, dexrazoxane and its analogues have been found to be toxic and as a result can only be used in relatively low dosages.

It will be appreciated that there thus exists a continuing need for compounds which are able to act as chemoprotectants during anti-cancer therapy.

In particular, there exists the need for an effective chemoprotectant which in reducing the toxic side effects of the anti-tumour agent, will permit higher, more effective doses of the anti-tumour agent to be administered.

The medical use of chelating agents and their metal chelates is well established, for example in diagnostic techniques such as X-ray, magnetic resonance imaging (MRI) ultrasound imaging or scintigraphy. A wide variety of chelating agents and metal chelates are known or have been described.

Aminopoly (carboxylic acid or carboxylic acid derivative) chelating agents and their metal chelates are well known and are described for example in EP-A-299795, EP-A-71564, DE-A-3401052, EP-A-203962 and EP-A-436579.

Dipyridoxyl based chelating agents and their chelates with trivalent metals have been described by Taliaferro (Inorg. Chem. 23: 1183–1192 (1984)). The compound N,N'-dipyridoxyl ethylenediamine-N,N'-diacetic acid (PLED) has been evaluated as a chelating agent for the preparation of gallium or indium containing radiopharmaceuticals (see Green et al. Int. J. Nucl. Med. Biol, 12(5): 381–386 (1985)).

A number of PLED derivatives and analogues have also been described for use in MRI contrast media, in particular the chelating agent N,N'-bis-(pyridoxal-5-phosphate)-ethylenediamine-N,N'-diacetic acid (DPDP) and its manganese (II) chelate, Mn DPDP (see EP-A-290047 and EP-A-292761).

BRIEF SUMMARY OF THE INVENTION

We have now found that certain chelating agents, in particular dipyridoxyl and aminopolycarboxylic acid based chelating agents, and their metal chelates are particularly effective in reducing the toxicity of anti-tumour agents, in particular anthracyclines and paclitaxel.

We have also found that certain manganese containing compounds are effective in reducing the toxicity of anti-tumor agents.

In one aspect the invention provides the use of a physiologically tolerable manganese compound or salt thereof, preferably having a molecular weight of less than 5000, more preferably less than 1000, e.g. less than 800, in the manufacture of a therapeutic agent for use in reducing the cardiotoxicity of an anti-tumour agent, e.g. an anthracycline drug and/or paclitaxel.

In another aspect the invention provides a method of reducing the cardiotoxicity of an anti-tumor agent administered to the human or non-human animal body, said method comprising administering to said body an anti-tumor agent and simultaneously, separately or sequentially a physiologically tolerable manganese compound or salt thereof, preferably having a molecular weight of less than 5000, more preferably less than 1000, e.g. less than 800.

Conveniently, the manganese compound may be present as a chelate, preferably having a $K_a$ in the range of from $10^9$ to $10^{25}$, more preferably $10^{10}$ to $10^{24}$, yet more preferably $10^{11}$ to $10^{23}$, e.g. $10^{12}$ to $10^{22}$. Particularly preferred chelates are those having a $K_a$ value smaller by a factor of at least $10^3$ than the $K_a$ value of the corresponding iron ($Fe^{3+}$) chelate.

In a second aspect the invention provides the use of a compound of formula I

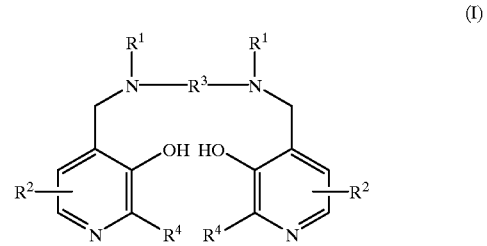

or a metal chelate or salt thereof in the manufacture of a therapeutic agent for use in reducing the cardiotoxicity of an anti-tumor agent, e.g. an anthracycline and/or paclitaxel (wherein in formula I each $R^1$ independently represents hydrogen or —$CH_2COR^5$;

$R^5$ represents hydroxy, optionally hydroxylated alkoxy, amino or alkylamido;

each $R^2$ independently represents a group $XYR^6$; X represents a bond, or a $C_{1-3}$ alkylene or oxoalkylene group optionally substituted by a group $R^7$;

Y represents a bond, an oxygen atom or a group $NR^6$;

$R^6$ is a hydrogen atom, a group $COOR^8$, an alkyl, alkenyl, cycloalkyl, aryl or aralkyl group optionally substituted by one or more groups selected from $COOR^8$, $CONR^8{}_2$, $NR^8{}_2$, $OR^8$, $=NR^8$, $=O$, $OP(O)(OR^8)R^7$ and $OSO_3M$;

$R^7$ is hydroxy, an optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation, e.g. an alkali or alkaline earth cation, an ammonium ion or an organic amine cation, such as a meglumine ion;

$R^3$ represents a $C_{1-8}$ alkylene group, preferably a $C_{1-6}$, e.g. a $C_{2-4}$ alkylene group, a 1,2-cycloalkylene group, or a 1,2-arylene group; and each $R^4$ independently represents hydrogen or $C_{1-3}$ alkyl).

Other chelators suitable for use in the method of the invention include the macrocyclic and more preferably linear or branched aminopolycarboxylic acid chelants of EP-A-299795, EP-A-71564, DE-A-3401052, EP-A-203962, EP-A-436579 and the phosphorus oxyacid analogs. Preferred chelating agents include DTPA and EDTA and amides thereof in which the nitrogens of the amide groups may be substituted by one or more $C_{1-18}$ alkyl groups, e.g. DTPA.BMA and EDTA.BMA.

As used herein the terms "alkyl" and "alkylene" include both straight-chained and branched, saturated and unsaturated hydrocarbons. The term "1,2-cycloalkylene" includes both cis and trans cycloalkylene groups and alkyl substituted cycloalkylene groups having from 5–8 carbon atoms. The term "1,2-arylene" includes phenyl and napthyl groups and alkyl substituted derivatives thereof having from 6 to 10 carbon atoms.

Unless otherwise specified, any alkyl, alkylene or alkenyl moiety may conveniently contain from 1 to 20, preferably 1–8, more preferably 1–6 and especially preferably 1–4 carbon atoms.

Cycloalkyl, aryl and aralkyl moieties may conveniently contain 3–18, preferably 5–12 and especially preferably 5–8 ring atoms. Aryl moieties comprising phenyl or naphthyl groups are preferred. As aralkyl groups, phenyl $C_{1-3}$ alkyl, especially benzyl, are preferred.

Where groups may optionally be substituted by hydroxy groups, this may be monosubstitution or polysubstitution and, in the case of polysubstitution, alkoxy and/or hydroxy substituents may be carried by alkoxy substituents.

In formula I, $R^5$ is preferably hydroxy, $C_{1-8}$ alkoxy, ethylene glycol, glycerol, amino or $C_{1-8}$ alkylamido. Preferably each group $R^1$ represents $—CH_2COR^5$ in which $R^5$ is hydroxy.

In the compounds of formula I, X is preferably a bond or a group selected from $CH_2$, $(CH_2)_2$, CO, $CH_2CO$, $CH_2CH_2CO$ or $CH_2COCH_2$. Preferably, Y represents a bond.

The compounds of formula I may have the same or different $R^2$ groups on the two pyridyl rings and these may be attached at the same or different ring positions. However, it is especially preferred that substitution be at the 5- and 6-positions, most especially the 6-position, i.e. para to the hydroxy group. Compounds in which the $R^2$ groups are identical and identically located, e.g. 6,6', are especially preferred.

Preferred as groups $R^6$ are mono- or poly(hydroxy or alkoxylated) alkyl groups or a group of the formula $OP(O)(OR^8)R^7$.

$R^7$ is preferably hydroxy or an unsubstituted alkyl or aminoalkyl group.

Particularly preferred identities for group $R^2$ include $CHR^7OCO(CH_2)_xPh$ and $CHR^7OCO(CH_2CO)_xPh$ (wherein x is 1 to 3), $CHR^7OCOBu^t$, $CH_2N(H)R^{6'}$, $CH_2N(R^{6'})_2$, $N(H)R^6$, $N(R^{6'})_2$, $CH_2OH$, $CH_2OR^{6'}$, $COOR^{6'}$, $CON(H)R^{6'}$, $CON(R^{6'})_2$ or $OR^{6'}$ (where $R^{6'}$ is a mono- or polyhydroxylated, preferably $C_{1-4}$, especially preferably $C_{1-3}$, alkyl group), $(CH_2)_nCOOR^7$ (wherein n is 1 to 6), $COOR^{7'}$ (where $R^{7'}$ is a $C_{1-4}$ alkyl, preferably $C_{1-3}$, especially preferably a methyl group), $CH_2OSO_3{}^-M$, $CH_2CH_2COOH$, $CH_2OP(O)(OH)(CH_2)_3NH_2$, $CH_2OP(O)(OH)CH_3$ or $CH_2OP(O)(OH)_2$ group. Yet more preferably, $R^2$ represents a group of the formula $CH_2OP(O)(OH)_2$.

Compounds of formula I in which $R^3$ is ethylene and $R^2$ has any of the identities listed above are particularly preferred.

Preferred metal chelates of the compounds for use in the method of the invention are those in which the metal ions are selected from the alkali and alkaline earth metals and from those metals having an atomic number from 22–31, 42, 44 and 58–70 and more particularly chelates having a $K_a$ in the range from $10^9$ to $10^{25}$, preferably $10^{10}$ to $10^{24}$, more preferably $10^{11}$ to $10^{23}$, e.g. $10^{12}$ to $10^{22}$. Particularly preferred chelates are those with metals other than iron which have a $K_a$ value smaller, preferably by a factor of at least $10^3$, than the $K_a$ value of the corresponding iron ($Fe^{3+}$) chelate. Suitable ions include $Na^+$, $Mn^{2+}$, $Cu^+$, $Cu^{2+}$, $Mg^{2+}$, $Gd^{3+}$, $Ca^{2+}$ and $Zn^{2+}$. $Mn^{2+}$ is especially preferred.

As chelates of aminopolycarboxylic acids, MnDTPA, MnEDTA, Mn DTPA.BMA and Mn EDTA.BMA are particularly preferred for use in accordance with the invention.

More particularly preferred for use in accordance with the invention is the compound N,N'-bis-(pyridoxal-5-phosphate)-ethylenediamine-N,N'-diacetic acid or N,N'-bis(3-hydroxy-2-methyl-5-phosphonomethyl-4-pyridylmethyl)-ethylenediamine-N,N'-diacetic acid (hereinafter referred to as DPDP) and the manganese (II) chelate, Mn(DPDP).

If not all of the labile hydrogens of the chelates are substituted by the complexed metal ion, biotolerability and/or solubility of the chelate may be increased by substituting the remaining labile hydrogen atoms with physiologically biocompatible cations of inorganic and/or organic bases or amino acids. Examples of suitable inorganic cations include $Li^+$, $K^+$, $Na^+$ and especially $Ca^{2+}$. Suitable organic cations include ammonium, substituted ammonium, ethanolamine, diethanolamine, morpholine, glucamine, N,N,-dimethyl glucamine, lysine, arginine or ornithine.

A particularly preferred use of the compounds herein described, in particular the chelating agents and their metal chelates, is as cardio-protective agents and such use extends not only to use in conjunction with drugs having cardiotoxic side effects, but also to the treatment or prevention of pathological conditions in which the heart is at risk. Thus, for example, the compounds in accordance with the invention may be used in the prevention or treatment of the cardiotoxic side effects of anti-tumour drugs, in particular the toxicity of anthracyclines, such as doxorubicin, and the toxicity of paclitaxel. In this regard, the compounds of the invention may be administered as a combined preparation with the anti-tumour drug. Alternatively, they may be administered separately, prior to, during or subsequent to administration of the anti-tumour drug.

As used herein the term "anthracyclines" includes natural and semi-synthetic anthracyclines, e.g. epirubicin, idarubicin, daunorubicin and, in particular, doxorubicin and salts thereof, as well as synthetic anthracyclines, e.g. mitoxantrone, and salts thereof.

Viewed from a further aspect the invention thus provides a pharmaceutical composition comprising a chelating agent according to the invention or a metal chelate or salt thereof, together with one or more anthracyclines, e.g. doxorubicin, and/or paclitaxel, and at least one pharmaceutically acceptable carrier or excipient.

Viewed from a yet still further aspect the invention provides a pack containing a chelating agent according to the invention or a metal chelate or salt thereof and separately an anthracycline and/or paclitaxel for simultaneous, separate or sequential use in anti-tumour therapy.

In another aspect the invention provides the use of a chelating agent according to the invention or a metal chelate or salt thereof together with one or more anthracyclines and/or paclitaxel in the manufacture of medicaments for simultaneous, separate or sequential administration in anti-tumour therapy.

In relation to the use of paclitaxel as the anti-tumor agent, it is preferable that patients are premedicated with steroids, antihistamines and/or $H_2$-antagonists to avoid hypersensitivity reactions, in particular anaphylactic reactions. Furthermore, myelotoxicity associated with paclitaxel administration, particularly with high doses of paclitaxel, can be substantially reduced by co-administration of granulocyte-colony stimulating factor (G-CSF), preferably given as a daily injection up to 24 hours after paclitaxel administration.

The compounds of the invention may be prepared by methods known in the art. Suitable methods for preparing the amino polycarboxylic acid based chelating agents are described in EP-A-299795, EP-A-71564, DE-A-3401052, EP-A-203962 and EP-A-436579.

In preparing the dipyridoxyl compounds, the compound PLED may e used as a starting material and may be appropriately derivatised using conventional procedures to obtain the compounds of formula I.

Suitable methods for preparing the compounds of formula I are described for example in EP-A-290047.

Alternatively the compounds of formula I may be prepared by reacting the corresponding pyridoxal compound with an alkylene diamine according to the procedure for making PLED described by Taliaferro (supra).

Alternatively, the compounds in accordance with the invention may be prepared by a process comprising one or more of the following steps:

(a) reacting a compound of formula II

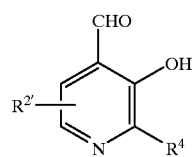
(II)

with a diamine of formula (III)

$H_2N-R^3-NH_2$ (III)

(wherein $R^3$ and $R^4$ are as hereinbefore defined and $R^{2'}$ is an optionally protected group $R^2$ as hereinbefore defined)

(b) hydrogenating a compound of formula (IV) obtained in step (a)

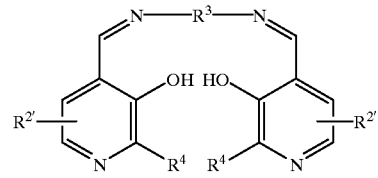
(IV)

(wherein $R^3$, $R^4$ and $R^{2'}$ are as hereinbefore defined)

(c) reacting a compound of formula (V)

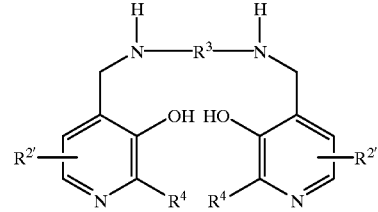
(V)

(wherein $R^3$, $R^4$ and $R^2$ are as hereinbefore defined) with a haloacetic, preferably bromoacetic, acid, and if necessary removing any protecting groups used; and (d) converting a compound of formula I into a chelate complex or salt thereof.

Pyridoxyl phosphate, pyridoxal and the other compounds of formula II and the alkylene diamine, cycloalkylene diamine and arylene compounds of formula III are well-known compounds readily available or can be readily synthesised by procedures well known in the art.

The reaction of step (a) may conveniently be performed in a suitable solvent, such as an alcohol (e.g. methanol) at a temperature in the range of from 0 to 60° C.

To obtain compounds of formula I where the $R^2$ groups are the same, a diamine of formula III may be reacted with two molar equivalents of a compound of formula II. For the preparation of compounds of formula I where the $R^2$ groups are different, the diamine of formula III is first reacted with a first compound of a formula II having a desired $R^{2'}$ group, and the reaction product thereby obtained is then reacted with a second compound of formula II bearing a different $R^{2'}$ group.

The hydrogenation of step (b) may be performed using conventional procedures, e.g. using a palladium or platinum catalyst.

The metal chelates for use in accordance with the invention may be formed by conventional procedures known in the art. In general, such processes involve disssolving or suspending a metal oxide or metal salt (e.g. nitrate, chloride or sulfate) in water or a lower alcohol such as methanol, ethanol, or isopropanol. To this solution or suspension is added an equimolar amount of the chelating agent in water or a lower alcohol and the mixture is stirred, if necessary with heating moderately or to the boiling point, until the reaction is completed. If the chelate salt formed is insoluble in the solvent used, the reaction product is isolated by filtering. If it is soluble, the reaction product is isolated by evaporating to dryness, e.g. by spray drying or lyophilising.

If acid groups such as the phosphoric acid groups are still present in the resulting chelate, it is advantageous to convert the acidic chelate salt into a neutral chelate salt by reaction with inorganic and/or organic bases or amino acids, which form physiologically acceptable cations, and to isolate them.

The carboxylic and phosphoric acid groups of the chelating agents can also be neutralised by esterification to prepare carboxylate and phosphate esters. Such esters can be prepared from the corresponding alcohols by conventional procedures known in the art. Suitable esters include, for example, esters of straight-chained or branched alcohols having from 1 to 18 carbon atoms, mono and polyhydric alkyl amino alcohols having from 1 to 18 carbon atoms, preferably having from 1 to 6 carbons, such as serinol or diethanolamine, and polyhydric alcohols having from 1 to 18 carbon atoms, such as ethylene glycol or glycerol.

Where the metal chelate carries an overall charge it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

The therapeutic agents of the present invention may be formulated with conventional pharmaceutical or veterinary formulation aids, for example stabilizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc. However, solutions, suspensions and dispersions in physiologically acceptable carrier media, for example water for injections, will generally be preferred.

The compounds according to the invention may therefore be formulated for administration using physiologically acceptable carriers or excipients in a manner well-known to those skilled in the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (e.g. tromethamine hydrochloride), additions (e.g. 0.01 to 10 mole percent) of chelants (such as, for example, DTPA, DTPA-bisamide or non-complexed chelants of formula I) or calcium chelate complexes (e.g. calcium DTPA, CaNaDTPA-bisamide, calcium salts or chelates of chelants of formula I), or, optionally, additions (e.g. 1 to 50 mole percent) of calcium or sodium salts (e.g. calcium chloride, calcium ascorbate, calcium gluconate or calcium lactate combined with metal chelate complexes of chelating agents according to the invention and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

The preferred mode for administering the metal chelates in accordance with the invention is parenteral, e.g. intravenous administration. Parenterally administrable forms, e.g. intravenous solutions, should be sterile and free from physiologically unacceptable agents, and should have low osmolality to minimize irritation or other adverse effects upon administration, and thus the compositions should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions may contain preservatives, antimicrobial agents, buffers and antioxidants conventionally used for parenteral solutions, excipients and other additives which are compatible with the chelates and which will not interfere with the manufacture, storage or use of the products.

The therapeutic agent in accordance with the invention, if in solution, suspension or dispersion form, will generally contain the chelant or metal chelate at a concentration in the range of from 0.0001 to 5.0 moles per liter, preferably 0.01 to 0.1 moles per liter. If convenient, the therapeutic agent may however be supplied in a more concentrated form for dilution prior to administration.

The therapeutic agent in accordance with the invention may conveniently be administered in amounts of from $10^{-2}$ to 100 $\mu$mol of the compounds per kilogram of body weight, e.g. about 10 $\mu$mol per kg bodyweight.

The present invention will now be illustrated further by the following non-limiting Examples and with reference to the attached figures.

DETAILED DESCRIPTION OF THE INVENTION

EXAMPLE 1

The protective effects of dexrazoxane, manganese chloride, DPDP, MnDPDP and ZnDPDP against doxorubicin were tested in the mouse left atrium model.

Method

Male mice were killed, the left atrium carefully dissected out, and hung in an organ bath filled with 37° C. Krebs Henseleit solution. Contractility was measured with a force transducer as described by van Acker et al. (Phlebology Suppl. 1: 31–32 (1993)). After equilibration, the atrium was preincubated with saline or various concentrations of MnDPDP for 30 minutes. Saline or 120 $\mu$M doxorubicin was subsequently added and the contractility measured for 60 minutes. Thereafter isoprenaline was added to test the capacity for positive inotropic action.

In another series of experiments male mice were injected intravenously with various doses of saline, dexrazoxane, manganese chloride, MnDPDP, ZnDPDP and DPDP. Fifteen or 30 minutes later the mice were killed and the in vitro part of the experiments was conducted as described above.

Results

Typical results are shown in FIGS. 1–4 attached hereto, and tabulated in Tables 1 and 2 below.

It can be seen that untreated controls (saline addition) contract to almost 100% of original force during the 60 minute measurement period, whereas the atria treated with doxorubicin display a marked negative inotropic effect, presumably due to the damage to isolated atrial muscle, leading to approx. 60% reduction in contractile force within 60 minutes.

Figure 1:
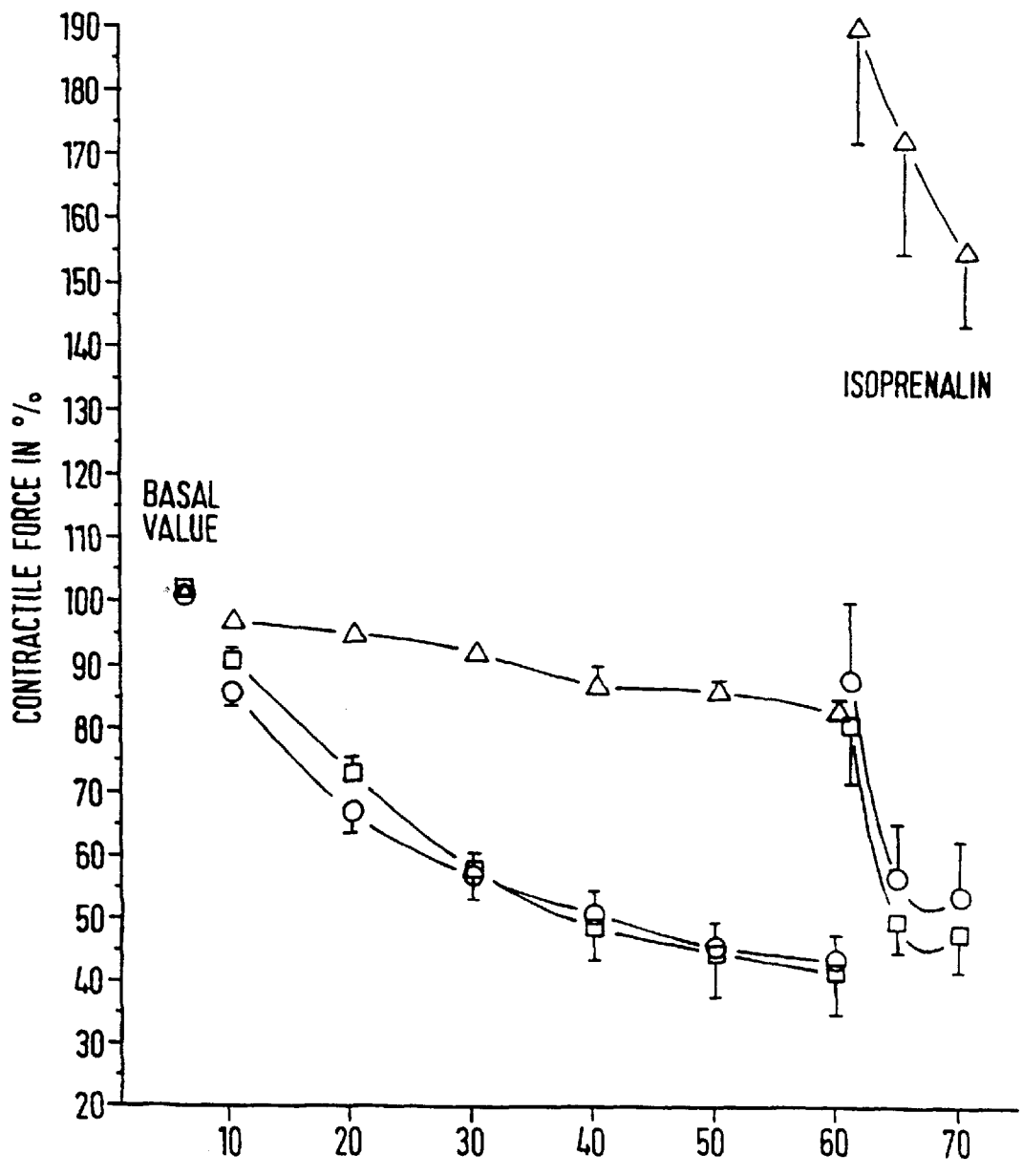
FIGS. 1–4 illustrate the effect of Doxorubicin on the contractile force of the mouse heart muscle following pretreatment with MnDPDP.
Figure 2:
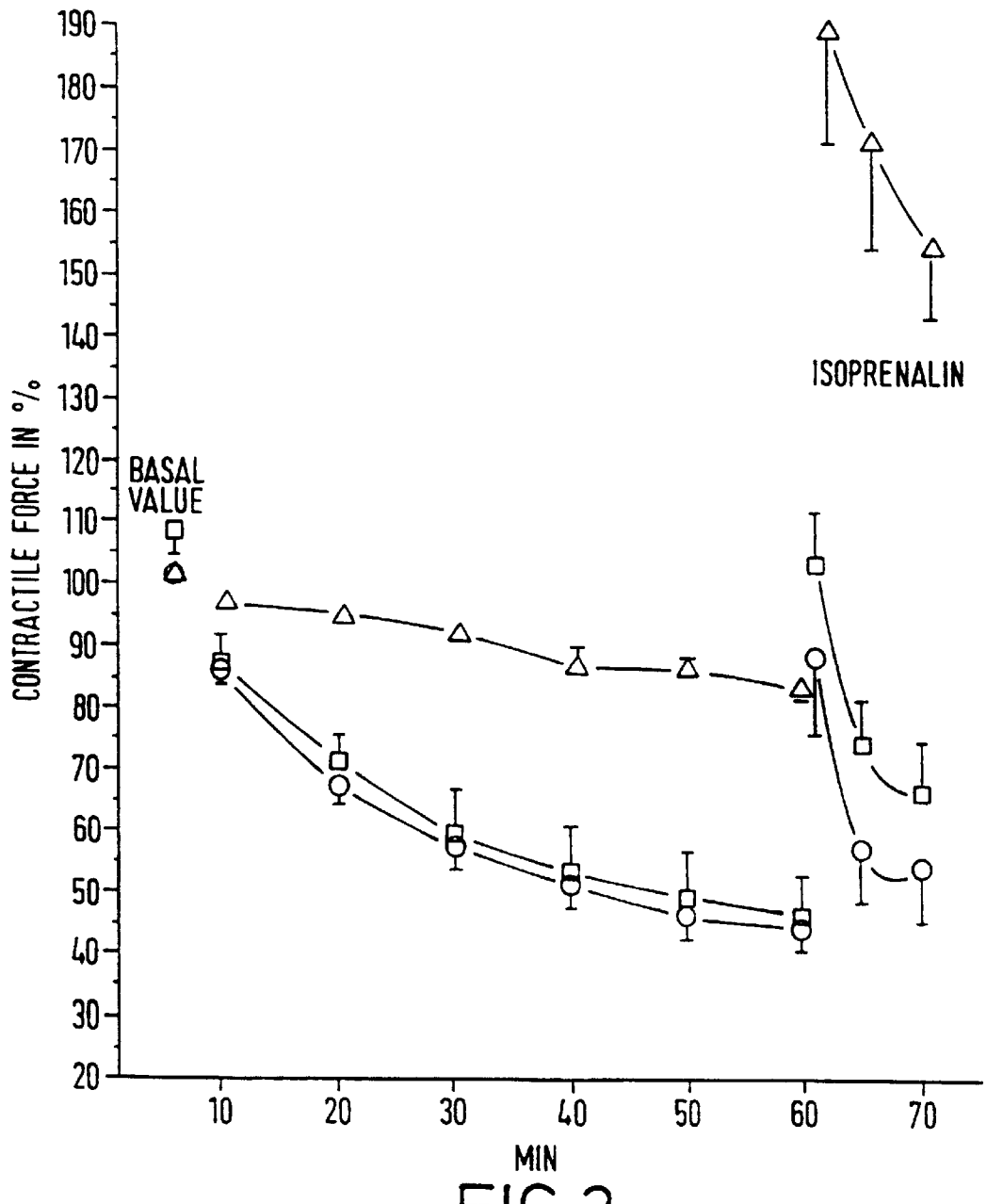
Figure 3:
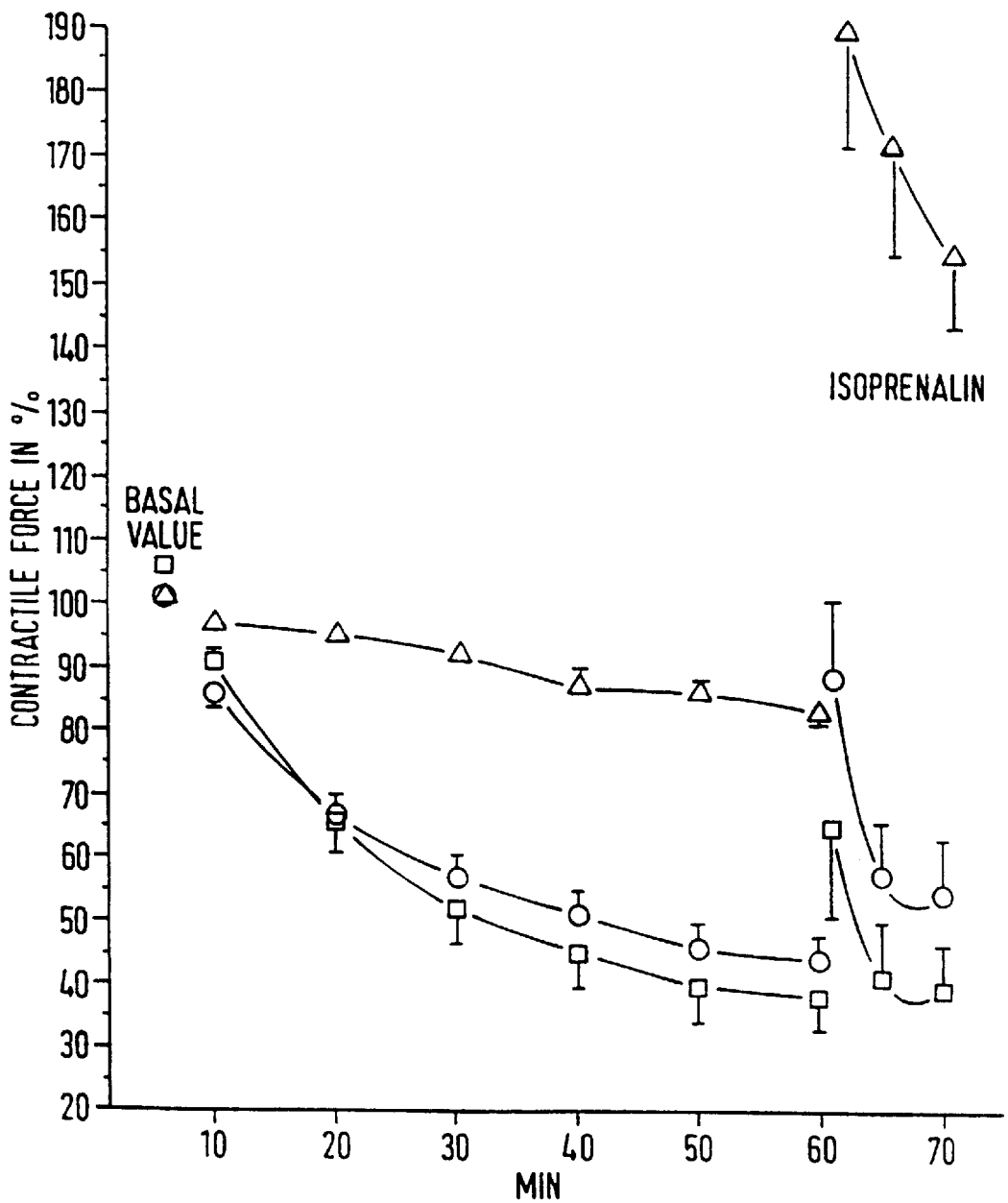
Figure 4:
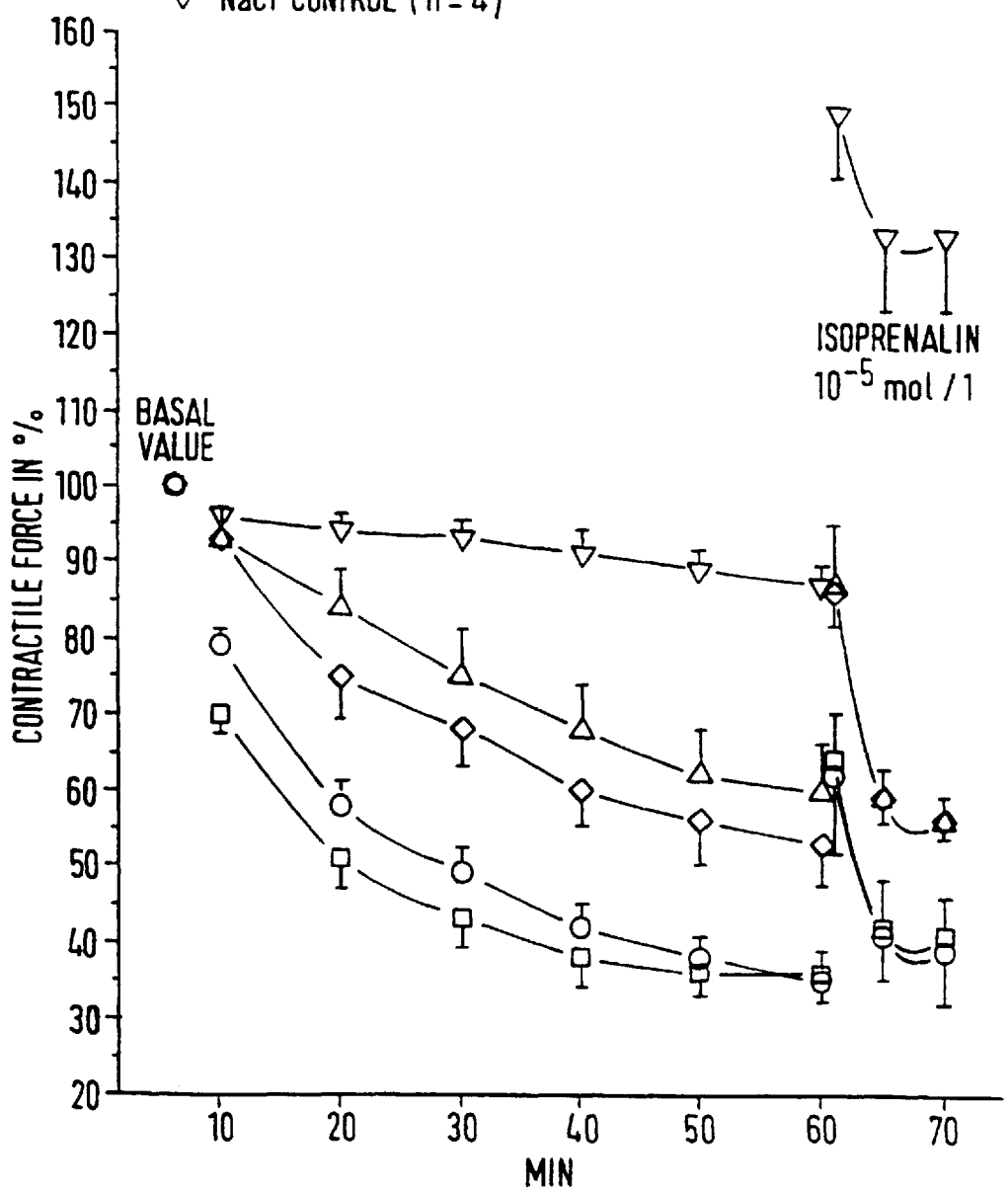

It is clear from FIGS. 1–3 that the manganese compound MnDPDP, when added directly into the organ bath, does not protect the heart muscle from deleterious effects of doxorubicin. However, it is clear from FIG. 4 that MnDPDP, when injected into the animal before the heart muscle is removed and placed in the organ bath, unexpectedly protects the heart muscle from the deleterious effects of doxorubicin. From Tables 1 and 2 it can be seen that either 15 or 30 minute pretreatment of the animal produces a 40–48% protection of the contractility. Equimolar doses of either manganese (as the chloride) or DPDP alone, although less effective still provide a degree of protection of the atrial muscle. The Zinc complex ZnDPDP also produced protective effects.

The reference compound dexrazoxane also protected against doxorubicin-induced cardiotoxicity in this test, although the quantities required were much larger (25–50 mg/kg·dexrazoxane=93–186 μmole/kg) compared to the effective doses of MnDPDP (1–10 μmole/kg).

TABLE 1

Protective effects of compounds against Doxorubicin-induced Cardiotoxicity Compound injected 15 minutes before removal of cardiac tissue

| Compound Tested | % protection* |
| --- | --- |
| Saline control | 0 |
| 1 μmole/kg MnDPDP | 16 |
| 10 μmole/kg MnDPDP | 40 |
| 30 μmole/kg MnDPDP | 4 |
| 100 μmole/kg MnDPDP | 0 |

*% protection is defined as % evaluation of contractile force when compared to doxorubicin + saline control.

TABLE 2

Protective effects of compounds against Doxorubicin-induced Cardiotoxicity Compounds injected 30 minutes before removal of cardiac tissue

| Compounds Tested | % protection* |
| --- | --- |
| Saline control | 0 |
| 1 μmole/kg MnDPDP | 35 |
| 10 μmole/kg MnDPDP | 48 |
| 30 μmole/kg MnDPDP | 2 |
| 1 μmole/kg DPDP | 6 |
| 10 μmole/kg DPDP | 15 |
| 30 μmole/kg DPDP | 10 |
| 1 μmole/kg ZnDPDP | 23 |
| 10 μmole/kg ZnDPDP | 33 |
| 30 μmole/kg ZnDPDP | 6 |
| 1 μmole/kg $MnCl_2$ | 17 |
| 10 μmole/kg $MnCl_2$ | 21 |
| 30 μmole/kg $MnCl_2$ | 28 |
| 25 mg/kg dexrazoxane | 43 |
| 50 mg/kg dexrazoxane | 47 |
| 100 mg/kg dexrazoxane | 0 |

*% protection is defined as % evaluation of contractile force when compared to doxorubicin + saline control.

EXAMPLE 2

The protective effects of saline, MnPLED, MnEDTA, MnDTPA.BMA, MnDTPA, EDTA and DTPA against doxorubicin were tested in another set of experiments.

Method

Male mice were injected intravenously with saline, 0.1 μmol/kg MnPLED, 10 μmol/kg MnEDTA, 10 μmol/kg MnDTPA.BMA, 10 μmol/kg MnDTPA, 10 μmol/kg EDTA or 10 μmol/kg DTPA.

Thirty minutes later the mice were killed, the left atrium carefully dissected out, and hung in an organ bath filled with 37° C. Krebs Henseleit solution. Contractility was measured as described in Example 1. After equilibration, saline or 60 μM doxorubicin was added and the contractility measured for 60 minutes.

Results

Figure 5:
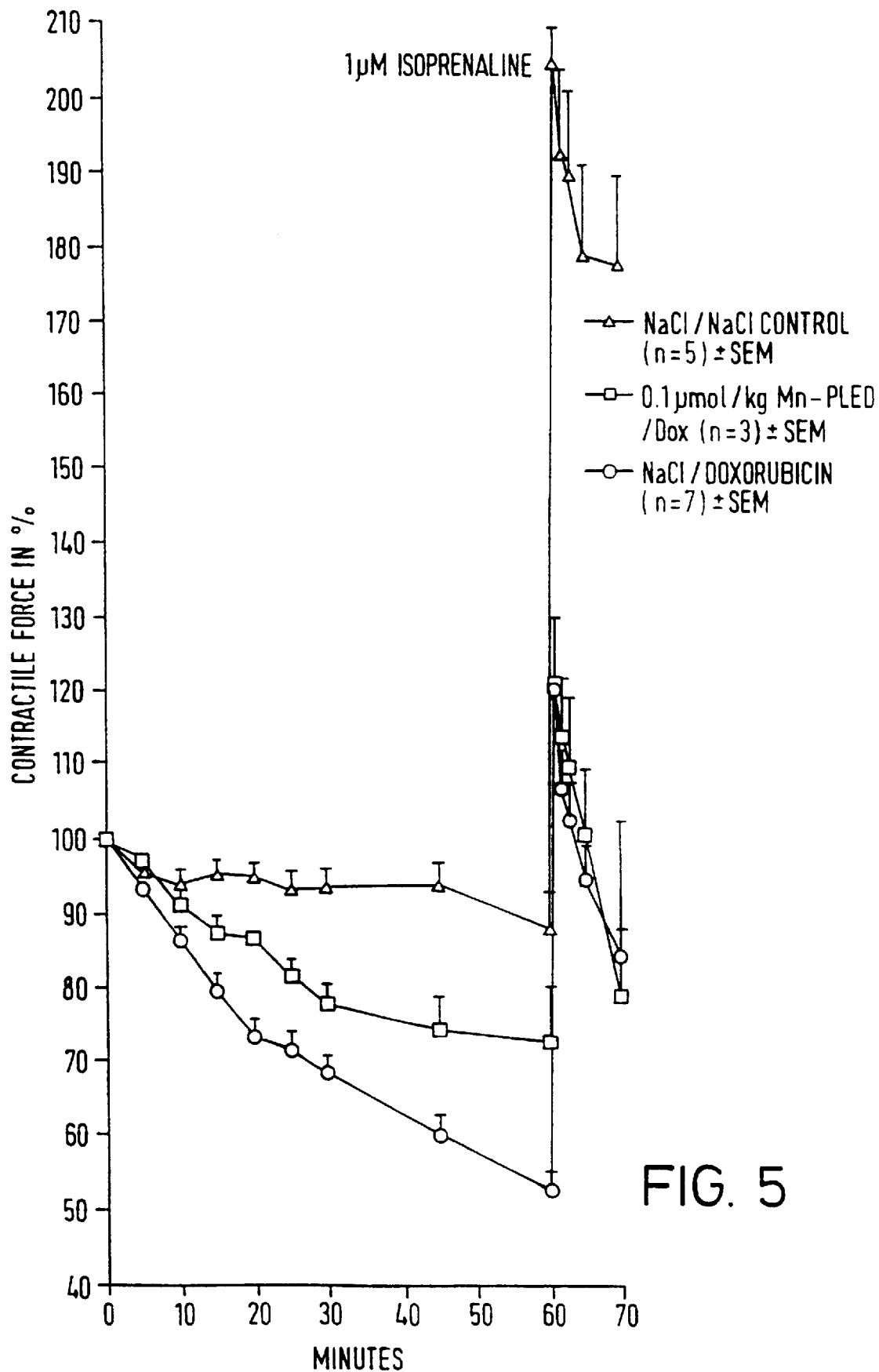
FIG. 5 illustrates the effect of Doxorubicin on the contractile force of the mouse heart muscle following pretreatment with MnPLED.

Typical results are shown in FIG. 5 attached hereto, and tabulated in Table 3 below.

It can be seen that atria treated with doxorubicin display a marked negative inotropic effect, presumably due to the damage to isolated atrial muscle, leading to approx. 60% reduction in contractile force within 60 minutes.

It is clear from FIG. 5 that 0.1 μmol/kg MnPLED, when injected into the animal before the heart muscle is removed and placed in the organ bath, protects the heart muscle from the deleterious effects of doxorubicin. From Table 3 it can be seen that 30 minute pretreatment with 0.1 μmol/kg MnPLED produces 56% protection of the atrial muscle, i.e. MnPLED is a ca. 100-fold more potent protector than MnDPDP (see Example 1). Pre-treatment with MnEDTA, MnDTPA, MnDTPA.BMA, EDTA and DTPA provide 42, 100, 12, 9 and 0% protection respectively. Whereas most of the tested manganese compounds gave effective protection, it is clear that equimolar doses of either EDTA or DTPA alone gave little or no protection.

TABLE 3

Protective effects of compounds against Doxorubicin-induced Cardiotoxicity Compounds injected 30 minutes before removal of cardiac tissue

| Compounds Tested | % protection* |
| --- | --- |
| Saline control | 0 (n = 7) |
| 0.1 μmol/kg MnPLED | 56 (n = 3) |
| 10 μmol/kg MnEDTA | 43 (n = 6) |
| 10 μmol/kg MnDTPA | 100 (n = 3) |
| 10 μmol/kg MnDTPA.BMA | 12 (n = 3) |
| 10 μmol/kg EDTA | 9 (n = 5) |
| 10 μmol/kg DTPA | 0 (n = 3) |

*% protection is defined as % evaluation of contractile force when compared to doxorubicin + saline control.

EXAMPLE 3

The protective effect of MnDPDP against daunomycin was tested in the mouse left atrium model.

Method

Male mice were injected intravenously with saline or 10 μmol/kg MnDPDP.

Thirty minutes later the mice were killed, the left atrium carefully dissected out, and hung in an organ bath filled with 37° C. Krebs Henseleit solution. Contractility was measured as described in Example 1. After equilibration, saline or 60 μmol/kg daunomycin was added to the organ bath and the contractility was measured for 60 minutes. Isoprenalin was added subsequently to test the tissue capacity for positive inotropic action.

Results

Figure 6:
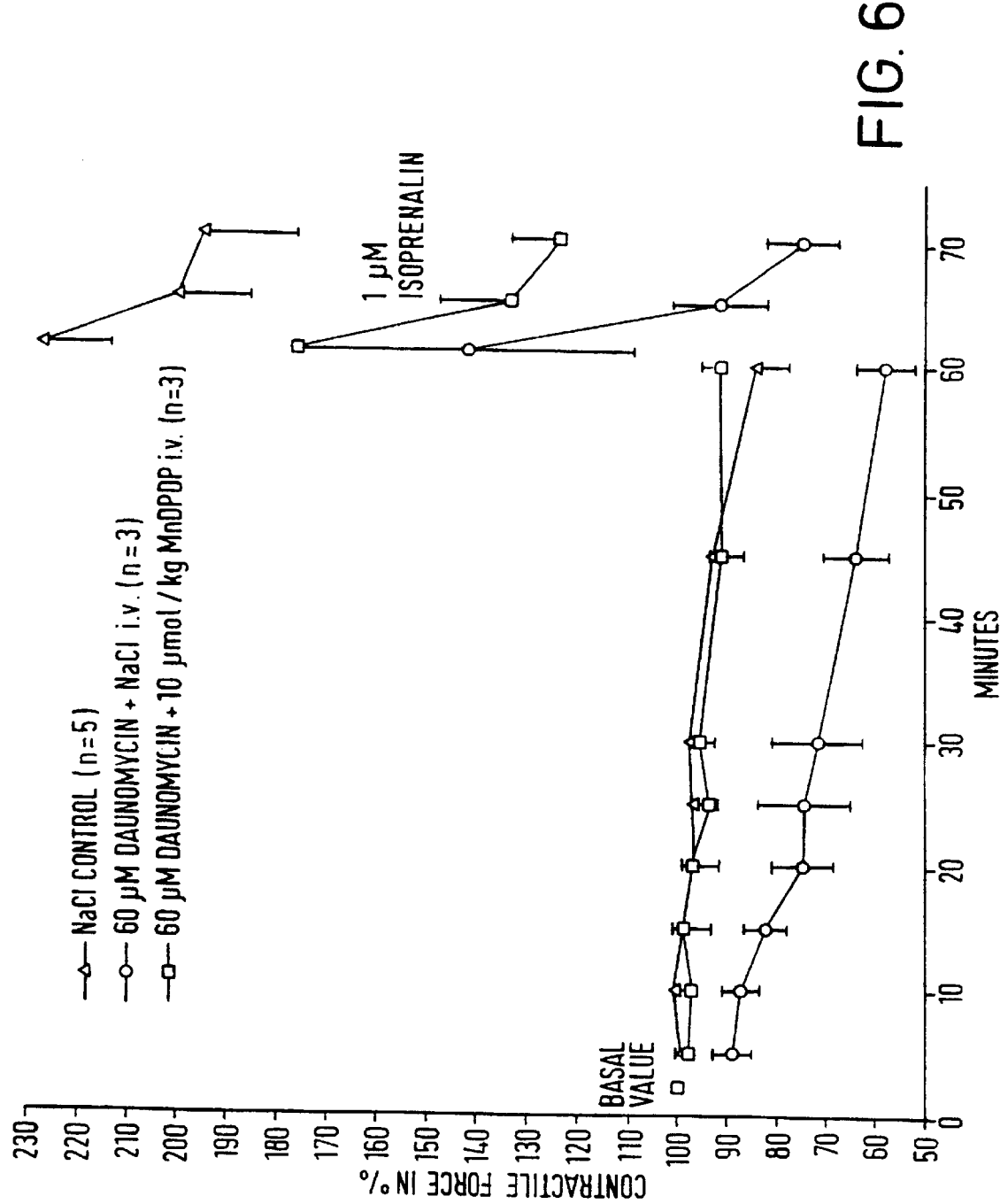
FIG. 6 illustrates the effect of Daunomycin on the contractile force of the mouse heart muscle following pretreatment with MnDPDP.

The results are shown in FIG. 6 attached hereto.

It can be seen that the untreated control (saline addition) contracted to almost 100% of original force during the 60 minute measurement period, whereas the muscles treated with daunomycin showed negative inotropic effects, leading to approx. 40% reduction of contractile force within 60 minutes. Pretreatment with 10 μmol/kg MnDPDP resulted in approx. 100% protection.

What is claimed is:

1. A method of reducing the cardiotoxicity of an anti-tumor agent administered to a human or non-human animal body, said method comprising administering to said body an anti-tumor agent and simultaneously, separately or sequentially a compound of formula I:

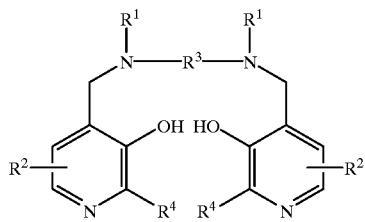

(I)

or a metal chelate thereof or salt of a metal chelate thereof wherein in formula I each $R^1$ independently represents hydrogen or —$CH_2COR^5$;

$R^5$ represents hydroxy, optionally hydroxylated alkoxy, amino or alkylamido;

each $R^2$ independently represents a group $XYR^6$;

X represents a bond, or a $C_{1-3}$ alkylene or oxoalkylene group optionally substituted by a group $R^7$;

Y represents a bond, an oxygen atom or a group $NR^6$;

$R^6$ is a hydrogen atom, a group $COOR^8$, an alkyl, alkenyl, cycloalkyl, aryl or aralkyl group optionally substituted by one or more groups selected from $COOR^8$, $CONR^8{}_2$, $NR^8{}_2$, $OR^8$, =$NR^8$, =O, $OP(O)(OR^8)R^7$ and $OSO_3M$;

$R^7$ is hydroxy, an optionally hydroxylated, optionally alkoxylated alkyl or aminoalkyl group;

$R^8$ is a hydrogen atom or an optionally hydroxylated, optionally alkoxylated alkyl group;

M is a hydrogen atom or one equivalent of a physiologically tolerable cation;

$R^3$ represents a $C_{1-8}$ alkylene group, a 1,2-cycloalkylene group, or a 1,2-arylene group; and each $R^4$ independently represents hydrogen or $C_{1-3}$ alkyl.

2. The method as claimed in claim 1 wherein said metal chelate comprises a metal ion selected from the group consisting of alkali and alkaline earth metals and metals having an atomic number of from 22–31, 42, 44 and 58–70.

3. The method as claimed in claim 2 wherein said metal ion is selected from the group consisting of $Na^+$, $Mn^{2+}$, $Cu^+$, $Cu^{2+}$, $Mg^{2+}$, $Gd^{3+}$, $Ca^{2+}$ and $Zn^{2+}$.

4. The method as claimed in claim 1 wherein said anti-tumor agent is an anthracycline drug and/or paclitaxel.

5. The method as claimed in claim 4 wherein said anthracycline drug is doxorubicin or daunomycin.

6. The method as claimed in claim 1 wherein said chelate is manganese chelate and has a $K_a$ in the range of from $10^9$ to $10^{25}$.

7. The method as claimed in claim 6 wherein said manganese chelate has a $K_a$ in the range of from $10^{12}$ to $10^{22}$.

8. The method as claimed in claim 1 wherein said chelate is manganese chelate and has a $K_a$ value smaller by a factor of at least $10^3$ than the $K_a$ value of the corresponding iron ($Fe^{3+}$) chelate.

* * * * *